(12) United States Patent
Wesselmann

(10) Patent No.: US 8,221,484 B2
(45) Date of Patent: Jul. 17, 2012

(54) MULTI-MEMBRANE BALLOON AND METHOD FOR MANUFACTURING A MULTI-MEMBRANE BALLOON

(75) Inventor: Matthias Wesselmann, Glattfelden (CH)

(73) Assignee: Biotronik VI Patent AG, Baar (CH)

( * ) Notice: Subject to any disclaimer, the term of this patent is extended or adjusted under 35 U.S.C. 154(b) by 766 days.

(21) Appl. No.: 12/359,580

(22) Filed: Jan. 26, 2009

(65) Prior Publication Data
US 2009/0192453 A1 Jul. 30, 2009

(30) Foreign Application Priority Data
Jan. 25, 2008 (DE) .................. 10 2008 006 092

(51) Int. Cl.
*A61M 29/02* (2006.01)
(52) U.S. Cl. ................................... 623/1.11
(58) Field of Classification Search ................ 623/1.11, 623/1.12, 1.15, 1.24, 1.46, 1.2; 606/191–198; 604/101.01, 101.02, 101.03
See application file for complete search history.

(56) References Cited

U.S. PATENT DOCUMENTS

| | | | |
|---|---|---|---|
| 5,087,394 A | 2/1992 | Keith | |
| 5,342,305 A | 8/1994 | Shonk | |
| 5,769,817 A | 6/1998 | Burgmeier | |
| 5,868,776 A | 2/1999 | Wright | |
| 6,123,712 A * | 9/2000 | Di Caprio et al. | 606/194 |
| 6,136,011 A * | 10/2000 | Stambaugh | 604/101.02 |
| 6,663,660 B2 * | 12/2003 | Dusbabek et al. | 623/1.11 |
| 6,986,785 B2 | 1/2006 | O'Shaughnessy et al. | |
| 7,947,207 B2 * | 5/2011 | McNiven et al. | 264/249 |
| 8,046,897 B2 * | 11/2011 | Wang et al. | 623/1.12 |

FOREIGN PATENT DOCUMENTS

| | | |
|---|---|---|
| EP | 0399712 A1 | 11/1990 |
| EP | 0834293 A1 | 4/1998 |
| EP | 0903121 A1 | 3/1999 |
| WO | 2007053967 A1 | 5/2007 |

OTHER PUBLICATIONS

Search Report for German Patent Application No. 10 2008 006 092.5; Oct. 28, 2008.
Search Report for European Patent Application No. 08171042.8; Jan. 27, 2009.

\* cited by examiner

*Primary Examiner* — Kevin T Truong
(74) *Attorney, Agent, or Firm* — Greer, Burns & Crain, Ltd.

(57) ABSTRACT

A multi-membrane balloon (10) for a catheter having an at least double membrane sleeve (20, 40) comprising at least one fillable and emptiable expansion space (46) between a proximal end (12) and a distal end (14), wherein a stiff supporting element (60) surrounds the at least double membrane sleeve (20, 40) and the outer membrane sleeve (20) surrounds one or more inner membrane sleeves (40). The supporting element (60) at least partially takes hold with the outer membrane sleeve (20).

22 Claims, 2 Drawing Sheets

MULTI-MEMBRANE BALLOON AND METHOD FOR MANUFACTURING A MULTI-MEMBRANE BALLOON

PRIORITY CLAIM

This patent application claims priority to German Patent Application No. 10 2008 006 092.5, filed Jan. 25, 2008, the disclosure of which is incorporated herein by reference in its entirety.

FIELD

The present disclosure relates to a multi-membrane balloon and a method for manufacturing a multi-membrane balloon.

BACKGROUND

Multi-membrane balloons are used in balloon catheters. One such use is for angioplasty, for example, in which balloon catheters are introduced into blood vessels, advanced up to a stenosis and dilated at the stenosis site to eliminate the constriction in the blood vessel. A guide wire having a small diameter usually protrudes beyond the balloon catheter at the distal end. The balloon catheter follows the guide wire and conforms to the shape of the respective blood vessel. It is problematic if the balloon bursts due to damage.

It is also known that a multi-membrane balloon may be surrounded by a stiff supporting element (a stent) which may remain in the area of the stenosis as a supporting structure. For example, one or both of the lumens of the membrane sleeves of the double membrane balloon that are arranged one inside the other may be filled with a gas or liquid, for example, and dilated whereupon the stent is dilated to a larger diameter. Such an insertion system for a stent having a multi-membrane balloon is described in U.S. Pat. No. 5,769,817, for example.

International Patent Publication No. WO 2007/053967 describes an insertion system for a stent in which balloon materials having a favorable gliding ability with respect to one another are used. To improve the gliding ability, a lubricant coating may be provided between the membrane layers. The gliding ability of the balloon membranes with respect to one another allows a better adaptability of the multi-membrane balloon to a specific shape of a hollow organ on insertion of the system. Both lumens may be dilated or the membrane balloon may be used as a double-walled design in which only the lumen of the inner balloon is dilated and/or inflated. The membrane layers are then in direct contact with one another and are mutually capable of gliding. For dilatation of the multi-membrane balloons, relatively high pressures are used and are between 50 and 60 bar with the insertion system described hereinbelow.

It is problematic that the stent which is placed around the single-membrane balloon or multi-membrane balloon can easily damage the outer membrane layer if the stent is compressed to a small diameter suitable for insertion of the stent after being pushed onto the balloon. If the balloon, which is not watertight, is dilated at the site of use, then, in the worst case, the stent may be opened only partially and may thus block the artery.

SUMMARY

The present disclosure describes several exemplary embodiments of the present invention.

One aspect of the present disclosure provides a multi-membrane balloon for a catheter having an at least double membrane sleeve, the multi-membrane balloon comprising at least one fillable and emptiable expansion space between a proximal end and a distal end, wherein the outer membrane sleeve surrounds one or more inner membrane sleeves, and wherein the outer membrane sleeve is closed at its distal end and at its proximal end.

Another aspect of the present disclosure provides a multi-membrane balloon for a catheter having an at least double membrane sleeve, the multi-membrane balloon comprising at least one fillable and emptiable expansion space between a proximal end and a distal end, whereby a stiff supporting element surrounds the at least double membrane sleeve, and the outer membrane sleeve surrounds one or more inner membrane sleeves, wherein the outer membrane sleeve at least partially takes hold with the supporting element.

A further aspect of the present disclosure provides a method for manufacturing a multi-membrane balloon for a catheter having an at least double membrane sleeve, the multi-membrane balloon comprising at least one fillable and emptiable expansion space between a proximal end and a distal end, whereby a stiff supporting element surrounds the at least double membrane sleeve, and the outer membrane sleeve surrounds one or more inner membrane sleeves, wherein the outer membrane sleeve at least partially takes hold with the supporting element, the method comprising dilating an outer membrane sleeve of the at least double membrane sleeve until the outer membrane sleeve at least partially takes hold with a supporting element that surrounds the outer membrane sleeve.

One aspect of the present disclosure provides a multi-membrane balloon which ensures a greater security on insertion and dilatation of the single-membrane balloon or multi-membrane balloon. In addition, a multi-membrane balloon with which the insertion of a stent into a hollow organ can be improved is provided. Furthermore, a method for producing a multi-membrane balloon is also provided.

The present disclosure provides a multi-membrane balloon for a catheter having at least a double membrane sleeve comprising at least one fillable and emptiable dilatable space between a proximal end and a distal end, whereby the outer membrane sleeve surrounds one or more inner membrane sleeves.

The outer membrane sleeve should be closed on its distal end and on its proximal end. Damage to the inner membrane sleeve, which should be dilated at the site of use, can then be compensated advantageously by the outer membrane sleeve. Because there are multiple layers, the outer membrane sleeve, and optionally also the inner membrane sleeve, may advantageously be designed to be very thin, e.g., up to 3 µm. The outer membrane sleeve forms a closed area which protects the one or more internal membrane sleeves. Even if there is a minor leakage (pinhole) in one of the outer membrane sleeves, the watertight feature of the inner membrane sleeve of the multi-membrane balloon may be utilized at the site of use. In the event of a bursting of the inner membrane sleeve (s), the energy thereby released can be dampened by the outer membrane sleeve thereby preventing damage to the tissue at the site of use. Breaks in a membrane sleeve cannot propagate into the other membrane sleeve(s).

The outer membrane sleeve may advantageously at least partially take hold with the supporting element that surrounds the membrane sleeve. The outer membrane sleeve may preferably be joined to the supporting element in a form-fitting manner. The pulling force on the supporting element can therefore be increased so that unwanted slippage of the supporting element from the membrane sleeve can be largely prevented.

The present disclosure also provides a multi-membrane balloon for a catheter having at least one double membrane sleeve comprising at least one fillable and emptiable expansion space between a proximal end and a distal end, whereby a rigid supporting element surrounds the at least double membrane sleeve and the outer membrane sleeve surrounds one or more inner membrane sleeves.

The outer membrane sleeve should at least partially take hold with the supporting element. The pulling force on the supporting element may be increased to advantage so that unintentional slippage of the supporting element off the membrane sleeve can be largely prevented. Due to the two or more membrane sleeves, it is possible to reliably prevent damage to the outer membrane sleeve from interfering with the effect of one or more inner membrane sleeves in dilatation at the site of use. Conversely, damage to the inner membrane sleeve to be dilated can be compensated by the outer membrane sleeve. Because multiple layers are used, the outer membrane sleeve, and optionally also the inner membrane sleeve, may advantageously be designed to be very thin, e.g., in the range of 3 µm.

The outer membrane sleeve may preferably be joined in a form-fitting manner to the supporting element. If the supporting element is designed with struts and interspaces, e.g., as a mesh material, the membrane sleeve may engage with nubs in the interspaces of the supporting element. In addition, to better adhesion of the supporting element on the membrane sleeve, the surrounding tissue may also be protected on insertion of the multi-membrane balloon into an organ or a blood vessel because the membrane sleeve that passes through the supporting element can easily adapt to the shape of the organ or the blood vessel. A buildup of pressure in dilatation of the multi-membrane balloon is accomplished through one or more inner membrane sleeves protected by the outer membrane sleeve.

In one exemplary embodiment of the present disclosure, the outer membrane sleeve may be sealed on its distal end and on its proximal end. The outer membrane sleeve, therefore, forms a closed area which protects the multiple inner membrane sleeve(s). Even if there is a minor leakage (pinhole) in one of the inner membrane sleeves, the imperviousness of the outer membrane sleeve of the multi-membrane balloon may be utilized at the site of use. If the inner membrane sleeve(s) burst(s), the energy thereby released can be dampened by the outer membrane sleeve thereby preventing damage to the tissue at the site of use. Breaks in a membrane sleeve cannot propagate into the other membrane sleeve.

The distal closure of the outer membrane sleeve in the axial direction may preferably be situated behind the distal closure of the one or more inner membrane sleeves without any overlap. The membrane sleeves remain movable with respect to one another. This is advantageous for the flexibility of the distal area of the instrument. This prevents the balloon membrane in the area of the cone and/or neck from forming a rigid tube due to overlapping closures. The distance between the closures preferably corresponds to 1 times the axial extent of the closure of the inner sleeve. As a result of this measure, the neck area of the multi-membrane balloon in which the closures are situated is very flexible. The closure may be formed by welding, for example. The bending torque can be reduced by separate closure of the outer multi-membrane, in particular, by welding.

An interspace between the outer membrane sleeve and the next internal membrane sleeve may advantageously have a pressure below atmospheric pressure. This allows proper embedding and stable fixation of the supporting element in the outer membrane sleeve.

The outer membrane sleeve may preferably have a greater bursting limit than the one or more internal membrane sleeves. In the event of bursting of an inner membrane sleeve which is exposed to a compressive load at the site of use, the outer membrane sleeve may dampen the energy thereby released, on the one hand. On the other hand, the outer membrane sleeve may also receive the medium thereby released. Damage to surrounding tissue at the site of use can therefore be prevented.

The outer membrane sleeve may be manufactured so that the one inner membrane sleeve or the multiple inner membrane sleeves have the same expansion state on dilatation. The drawing ratios in producing the multi-membrane balloon, preferably by blow-molding, can be adjusted easily, e.g., by means of hoop drawing, i.e., drawing in the circumferential area. This also allows a homogeneous stress distribution in the multi-membrane balloon in the individual membrane sleeves even under a full load. For purposes of the present disclosure, a full load denotes an increase in the circumference of the membrane sleeve by a multiple of its initial circumference on insertion. The stress distribution in the balloon cross section can be homogenized.

The outer membrane sleeve may have a protective layer which protects the membrane sleeve from damage in at least some areas on its outside.

The outer membrane sleeve may preferably have a larger volume than the one or more inner membrane sleeves in the regular dilated state. It is, therefore, possible to ensure that rupturing of the inner membrane sleeve(s) will at any rate occur before rupturing of the outer membrane sleeve.

The present disclosure also provides a method for manufacturing a multi-membrane balloon having an at least double membrane sleeve, in which an outer membrane sleeve of the at least double membrane sleeve is dilated until the outer membrane sleeve at least partially takes hold with the supporting element surrounding the outer membrane sleeve.

The outer membrane sleeve may preferably be attached to the supporting element in a form-fitting manner. This may be accomplished easily by dilatation of the outer membrane sleeve until the membrane sleeve dilates into the interspaces of the supporting element.

The supporting element attached to the outer membrane sleeve may be compressed to a desired smaller diameter. This advantageously yields a smaller diameter of the entire arrangement thereby simplifying insertion of the multi-membrane balloon into a hollow organ. The supporting element is preferably crimped to the desired smaller diameter.

In another exemplary embodiment of the method, the outer membrane sleeve may be closed on its open end. This is preferably accomplished by welding.

In a further exemplary embodiment, the membrane sleeve may first be evacuated and then closed at its open end. In this way, the supporting element may be secured especially reliably on this membrane sleeve through the parts of the outer membrane sleeve that engage in these interspaces.

The membrane sleeves may preferably be manufactured in such a way that, in the dilated state, the membrane sleeves assume a uniform expansion state. In this way, a homogenization of the stress distribution over the circumference of the membrane sleeves can be achieved during operation.

BRIEF DESCRIPTION OF THE DRAWINGS

Various aspects of the present disclosure are described hereinbelow with reference to the accompanying figures.

DETAILED DESCRIPTION

Figure 1:
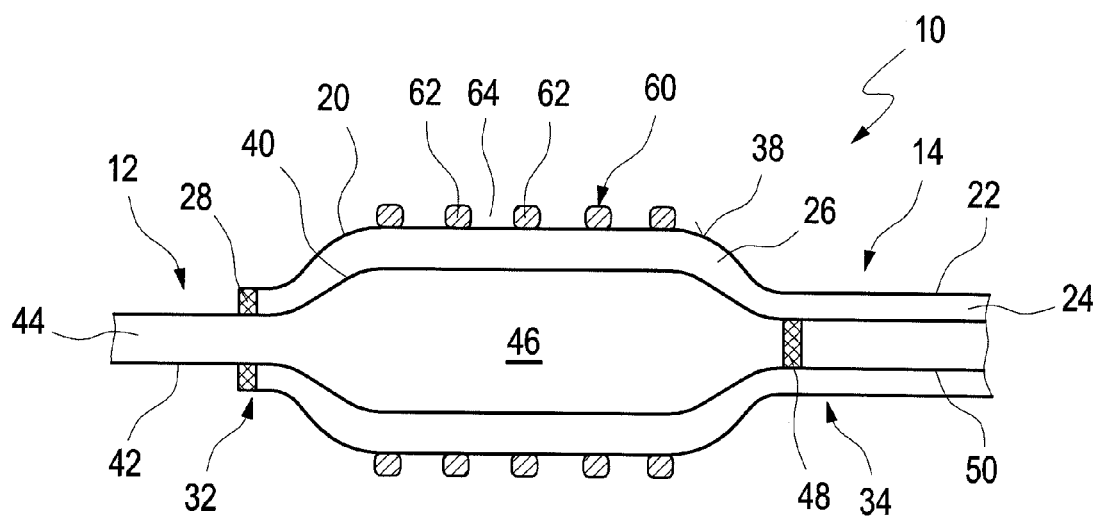
FIG. 1 is a schematic side cross-section view of one exemplary embodiment of a double membrane balloon in a first condition.

In the figures, functionally identical elements or those having the same effect are labeled with the same reference numerals. The figures are schematic diagrams of the present disclosure. The figures illustrate nonspecific parameters of the present disclosure. In addition, the figures show only exemplary embodiments of the present disclosure and should not restrict the invention to the exemplary embodiments depicted herein.

Figure 2:
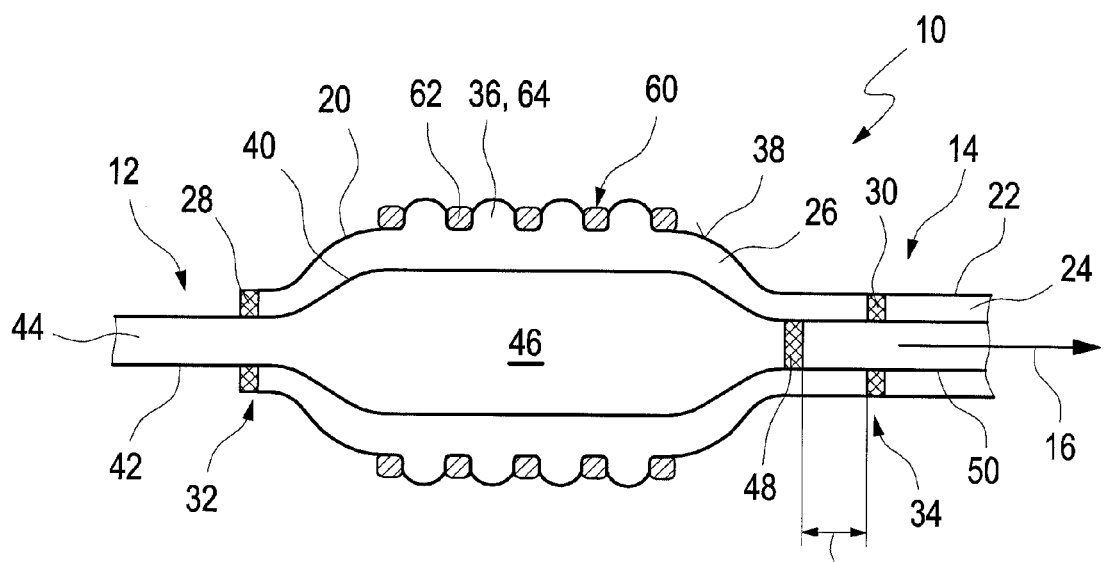
FIG. 2 is a schematic side cross-section view of the double membrane balloon shown in FIG. 1 in a second condition.

FIGS. 1 and 2 show a section through a first exemplary embodiment of a multi-membrane balloon 10, which is shown as a double membrane balloon, as an example, surrounded by a supporting element 60 (stent) in two different process steps of a preferred manufacturing method. FIG. 1 shows the double membrane balloon (labeled as 10 in the remaining disclosure) in a first process step during production with a loose supporting element 60. FIG. 2 shows the double membrane balloon 10 with the attached supporting element 60. The membrane sleeves 20, 40 may be made of conventional suitable materials such as rubber or plastic, e.g., polyamide (nylon), polyester, e.g., polyethylene terephthalate (PET).

The double membrane balloon 10 comprises an outer membrane sleeve 20, which is closed at one end according to the process step illustrated herein and in which an inner membrane sleeve 40 which is closed at one end is arranged, the membrane sleeve having a fillable and emptiable expansion space 46 between a proximal end 12 and a distal end 14 of the double membrane balloon 10. The outer membrane sleeve 20 is arranged at a distance from the inner membrane sleeve 40 with an interspace 26. The outer membrane sleeve 20 may be coated with a protective layer 38 on the outside to improve the friction properties, for example, and/or also to protect the membrane sleeve 20 from damage.

The inner membrane sleeve 40 is closed on the distal end 14 and the outer membrane sleeve 20 is closed on its end 32 facing the proximal end 12 and is in tight contact with a tube 42 at a closure 28. The closure 28 can be produced by welding, for example. The rigid supporting element 60 surrounds the double membrane sleeve 20, 40.

The tube 42 is arranged on the inner membrane sleeve 40 on the proximal end 12. At the site of use, the inner membrane sleeve 40 and/or its expansion space 46 may be inflated with a suitable medium inflated through a hollow space 44 of the tube 42 and, consequently, the double membrane balloon 10 can be dilated. The inner membrane sleeve 40 is sealed with a closure 48 on the distal end 14. The closure 48 may be formed by welding, for example. A tube 50 in which a guide wire or other components, for example, are arranged (not shown) is adjacent to the closure 48.

The outer membrane sleeve 20 is still open on its end 34 facing the distal end 14 in the process step depicted in FIG. 1, and the outer membrane sleeve 20 develops into a tube 24, which has a hollow space 24 and surrounds the tube 50.

The outer membrane sleeve 20 may advantageously have a higher bursting limit than the one or several inner membrane sleeve(s) 40 so that in the worst case of a sleeve breakage of the inner membrane sleeve 40, the membrane sleeve 20 can remain stable.

The outer membrane sleeve 20 may be manufactured in such a way that in dilatation of the inner membrane sleeve 40, the outer membrane sleeve 20 has the same elongation state as the inner membrane sleeve 40. Thus the multi-membrane balloon 10 is very stable per se and the favorable strength-increasing properties of the double- and/or multi-membrane sleeves can be utilized because the inner and outer membrane sleeves 40, 20 can now be stretched uniformly.

The outer membrane sleeve 20 may expediently have a larger volume than the one inner membrane sleeve 40 in the regular dilated state so that if the inner membrane sleeve 40 bursts, the contents of the inner membrane sleeve 40 can be received reliably by the outer membrane sleeve 20.

According to an exemplary process step of the method of the present disclosure, which is diagrammed in FIG. 2, the outer membrane sleeve 20 is inflated and/or dilated until the outer membrane sleeve 20 at least partially takes hold with the supporting element 60 surrounding the outer membrane sleeve 20, preferably until the outer membrane sleeve 20 is in form-fitting contact with the supporting element 60. The outer membrane sleeve 20 then protrudes into interspaces 64 in struts 62 of the supporting element 60 in the manner of nubs or folds 36.

After the supporting element 60 has been embedded in the outer membrane 20, the supporting element 60 may be compressed, e.g., by crimping, to a desired smaller diameter which the supporting element 60 should assume for insertion to the site of use, for example. The multi-membrane balloon 10 makes a distal balloon lumen available for dilatation of the outer membrane sleeve 20 for the crimping process in the form of the tube 24. The distal balloon lumen is closed off and separated after successful embedding of the support organ 60 close to the balloon.

The outer membrane sleeve 20 protrudes in the manner of folds or nubs 36 into the interspaces 64 of struts 62 of the supporting element 60. The supporting element 60, therefore, sits in an especially stable manner on the multi-membrane balloon 10 and has a high resistance to being stripped off thereby greatly increasing the pull-away force to pull the supporting element 60 away from the multi-membrane balloon 10. If the multi-membrane balloon 10 is dilated to its insertion diameter at the site of use by passing a suitable medium into the expansion space 46 of the inner membrane sleeve 40, the outer membrane sleeve 20 and the supporting element 60 are also dilated. When the ideal diameter of the supporting element 60 has been reached, the expansion space 46 can be emptied again so that the supporting element 60 can then easily be stripped away from the multi-membrane balloon 10.

After embedding and compressing the supporting element 60, the outer membrane sleeve 20 may be closed and severed at its open end 24. It is advantageous if the membrane sleeve 20 and/or the interspace 26 is/are evacuated in advance. The struts 62 of the supporting element 60 are, therefore, secured especially well between the nubs 36 of the outer membrane sleeve 20. Due to the fact that the compressed supporting element 60 is embedded in the outer membrane sleeve 20, the supporting element 60 and the outer membrane sleeve 20 form a relatively thick protective sheathing for the inner membrane sleeve 40 so that in handling the multi-membrane balloon 10, the inner membrane sleeve 40 is protected especially well.

In closing the outer membrane sleeve 20 in its distal end 34, preferably the distal closure 30 of the outer membrane sleeve 20 is arranged behind a distal closure 48 of the inner membrane sleeve 40 in the axial direction 16. This results in the multi-membrane balloon 10 being very flexible in the neck area. If the closures 48 of the inner membrane sleeves 40 and 30 of the outer membrane sleeve 20 were in contact with one another, this area of the multi-membrane balloon 10 would be very stiff.

It is favorable if the distal closure 30 of the outer membrane sleeve 20 is a distance 52 behind the distal closure 48 of the inner membrane sleeve 40 in the axial direction 16, the distance corresponding at least to 1 times the axial extent, preferably at least double the axial extent of the closure 30.

Figure 3:
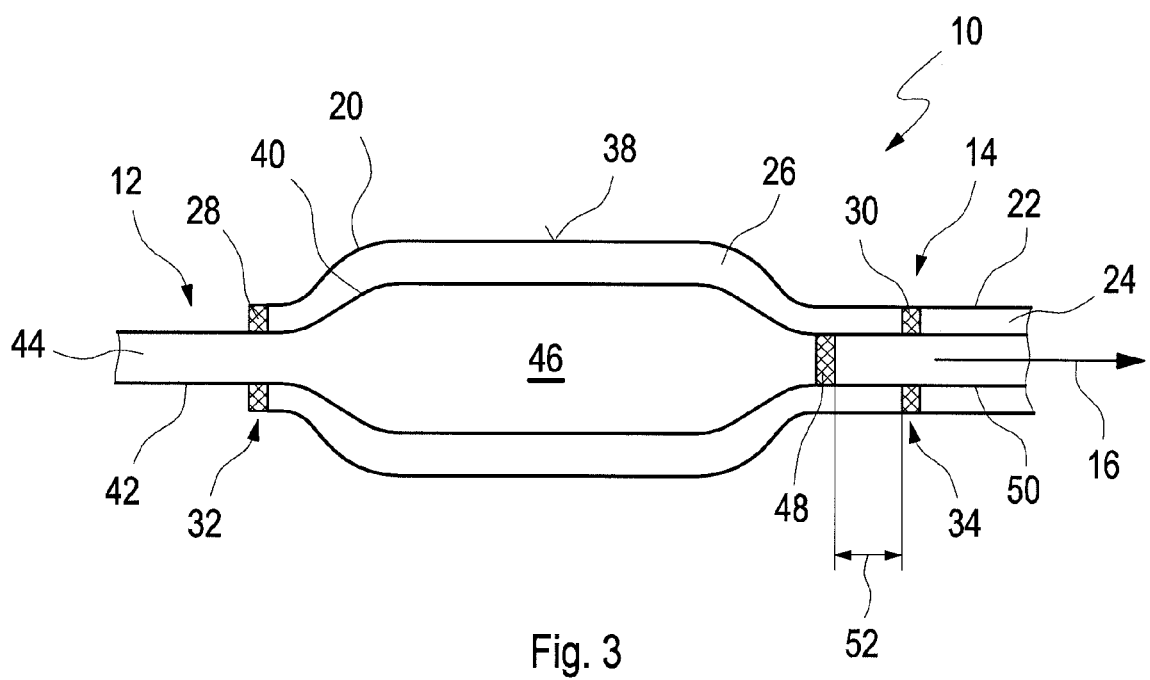
FIG. 3 is a schematic side cross-section view of a second exemplary embodiment of a double membrane balloon.

Another exemplary embodiment of the present disclosure is depicted in FIG. 3. The design of the multi-membrane balloon 10 corresponds to that shown in FIGS. 1 and 2. In contrast, however, no supporting element is provided which would surround the multi-membrane balloon 10. To avoid unnecessary repetition, therefore, reference is made to the previous description of figures regarding any details that have not been explained but are present in both diagrams of the multi-membrane balloon 10.

The outer membrane sleeve 20 is closed at its distal end 32 and its proximal end 34. The distal closure 30 of the outer membrane sleeve 20 is situated behind a distal closure 48 of the inner membrane sleeve 40 in the axial direction 16.

The distal closure 30 of the outer membrane sleeve 20 in the axial direction 16 is advantageously at a distance 52 behind the distal closure 48 of the inner membrane sleeve 40 which preferably corresponds to at least 1 times the axial extent of the closure 30. Due to the axial offset, the neck area of the multi-membrane balloon 10 with the closures 48 and 30 is very flexible and may easily be adapted to curvatures. Insertion to the site of use may, therefore, be simplified.

Again, in this exemplary embodiment, an interspace 26 between the outer membrane sleeve 20 and the inner membrane sleeve 40 may be evacuated to impart more stability to the arrangement and to provide mechanical protection for the inner membrane sleeve 40.

All patents, patent applications and publications referred to herein are incorporated by reference in their entirety.

What is claimed is:

1. A multi-membrane balloon for a catheter, comprising: at least two membrane sleeves at least one of which defines an inner membrane sleeve and one of which defines an outer membrane sleeve, each sleeve having a proximal end and a distal end and at least one expandable and collapsible expansion space portion defined between the proximal and distal ends of each membrane sleeve, the expansion space of the outer membrane sleeve substantially surrounding the expansion space of the at least one inner membrane sleeve, wherein the outer membrane sleeve distal end forms a substantially fluid tight seal around the proximal end of the outermost inner membrane sleeve, the at least one inner membrane sleeve distal end is closed.

2. The multi-membrane balloon of claim 1, wherein at least a portion of the outer membrane sleeve is either proximate to or in contact with a supporting element surrounding at least a portion of the outer membrane sleeve.

3. The multi-membrane balloon of claim 2, wherein the outer membrane sleeve contacts the supporting element in a form-fitting manner when at least a portion of the outer membrane sleeve is expanded.

4. The multi-membrane balloon of claim 1, further comprising a protective layer on the outside of at least a portion of the outer membrane sleeve outside and a protective layer on the inside of at least a portion of the inner membrane sleeve.

5. The multi-membrane balloon of claim 1, wherein the outer membrane sleeve has a larger volume than the one or more inner membrane sleeves in a regular dilated state.

6. A multi-membrane balloon for a catheter having a plurality of membrane sleeves, the multi-membrane balloon comprising at least one fillable and emptiable expansion space defined between a proximal end and a distal end of the plurality of membrane sleeves, a stiff supporting element surrounding at least a portion of the plurality of membrane sleeves, the outer membrane sleeve surrounding one or more inner membrane sleeves, wherein the outer membrane sleeve at least partially contacts the supporting element, wherein the outer membrane sleeve distal end forms a substantially fluid tight seal around the proximal end of the outermost inner membrane sleeve, and the at least one inner membrane sleeve distal end is closed.

7. The multi-membrane balloon of claim 6, wherein the outer membrane sleeve has a form-fitting connection to the supporting element whereby portions of the outer membrane sleeve form crenations between spaces existing in the supporting element.

8. The multi-membrane balloon of claim 6, wherein the outer membrane sleeve proximal end forms a substantially fluid tight seal around the distal end of the outermost inner membrane sleeve.

9. The multi-membrane balloon of claim 1, wherein the distal closure of the outer membrane sleeve is situated behind a distal closure of the one or more inner membrane sleeves in the axial direction.

10. The multi-membrane balloon of claim 9, wherein the distal closure of the outer membrane sleeve is situated behind the distal closure of the one or more inner membrane sleeves in the axial direction with a distance and without any overlap.

11. The multi-membrane balloon of claim 1, wherein an interspace defined between the outer membrane sleeve and the closest inner membrane sleeve has a pressure below atmospheric pressure.

12. The multi-membrane balloon of claim 1, wherein the outer membrane sleeve has a higher bursting limit than the one or more inner membrane sleeves.

13. The multi-membrane balloon of claim 1, wherein the outer membrane sleeve has substantially the same elongation state when the one or more inner membrane sleeves are dilated.

14. The multi-membrane balloon of claim 6, further comprising a distal balloon volume for dilation of the outer membrane sleeve so as to crimp at least a portion of the supporting element.

15. A method for manufacturing a multi-membrane balloon for a catheter having an at least double membrane sleeve, comprising:
  (a) providing at least two membrane sleeves at least one of which defines an inner membrane sleeve and one of which defines an outer membrane sleeve, each sleeve having a proximal end and a distal end and at least one expandable and collapsible expansion space portion defined between the proximal and distal ends of each membrane sleeve, the expansion space of the outer membrane sleeve substantially surrounding the expansion space of the at least one inner membrane sleeve, wherein the outer membrane sleeve distal end forms a substantially fluid tight seal around the proximal end of the outermost inner membrane sleeve, the at least one inner membrane distal end sleeve is closed; and
  (b) dilating the outer membrane sleeve of the at least double membrane sleeve until the outer membrane sleeve at least partially contacts a supporting element that at least partially surrounds the outer membrane sleeve.

16. The method of claim 15, wherein the outer membrane sleeve contacts the supporting element in a form-fitting manner.

17. The method of claim 15, further comprising:
   (c) compressing the supporting element to a desired smaller diameter.

18. The method of claim 15, further comprising sealing the proximal end of the outer membrane sleeve around the distal end of the outermost inner membrane sleeve.

19. The method of claim 15, further comprising evacuating the outer membrane sleeve and sealing the outer membrane sleeve proximal end.

20. The method of claim 15, wherein the multi-membrane balloon has a distal balloon volume for dilation of the outer membrane sleeve for a crimping operation of the supporting element.

21. The method of claim 20, further comprising closing the distal balloon volume and shortening after embedding the supporting element.

22. The method of claim 15, wherein the inner and outer membrane sleeves are manufactured so that in the dilated state the membrane sleeves have a uniform state of elongation.

* * * * *